(12) United States Patent
Reinhart et al.

(10) Patent No.: US 7,299,701 B2
(45) Date of Patent: Nov. 27, 2007

(54) COMPRESSIVE FATIGUE AND ENERGY TEST APPARATUS AND METHOD FOR TESTING CLUTCH PLATE FRICTION MATERIALS

(75) Inventors: Timothy J. Reinhart, Brownsburg, IN (US); Kerry W. Stadtfeld, Greenwood, IN (US)

(73) Assignee: General Motors Corporation, Detroit, MI (US)

( * ) Notice: Subject to any disclaimer, the term of this patent is extended or adjusted under 35 U.S.C. 154(b) by 127 days.

(21) Appl. No.: 11/233,842

(22) Filed: Sep. 23, 2005

(65) Prior Publication Data

US 2007/0068271 A1    Mar. 29, 2007

(51) Int. Cl.
  *G01L 1/00* (2006.01)
(52) U.S. Cl. .............................. 73/766; 73/104; 73/105; 73/118.1
(58) Field of Classification Search .................. 73/104, 73/105, 118.1, 766
See application file for complete search history.

(56) References Cited

U.S. PATENT DOCUMENTS

| | | | | |
|---|---|---|---|---|
| 4,993,531 A | * | 2/1991 | Villata | 192/107 C |
| 5,003,817 A | * | 4/1991 | Pflaum et al. | 73/118.1 |
| 5,005,985 A | * | 4/1991 | Piorkowska-Galeska et al. | 374/44 |
| 5,685,193 A | * | 11/1997 | Hurtubise et al. | 73/150 A |
| 5,689,058 A | * | 11/1997 | Yuan | 73/9 |
| 5,731,975 A | * | 3/1998 | Nakashima | 701/83 |
| 5,823,912 A | * | 10/1998 | Fischer et al. | 477/97 |
| 6,132,082 A | * | 10/2000 | Pause | 374/43 |
| 6,330,820 B1 | * | 12/2001 | Cotterill et al. | 73/9 |
| 6,601,457 B2 | * | 8/2003 | Li et al. | 73/818 |

* cited by examiner

*Primary Examiner*—Edward Lefkowitz
*Assistant Examiner*—Freddie Kirkland, III

(57) ABSTRACT

The present invention presents a means for simultaneously testing the compressive strength and measuring the thermal energy dissipated by a given friction material during slip. The testing apparatus includes a rotatable flywheel that rotates a transmission reaction plate to simulate a typical reaction plate in a vehicle transmission assembly. A plurality of test samples selectively interact with the reaction plate while being elevated by hydraulically actuated cylinders. The thermal energy dissipated between the reaction plate and each test sample is measured for each test sample. A method for accomplishing the same for a bill-of-design reference is also included.

16 Claims, 3 Drawing Sheets

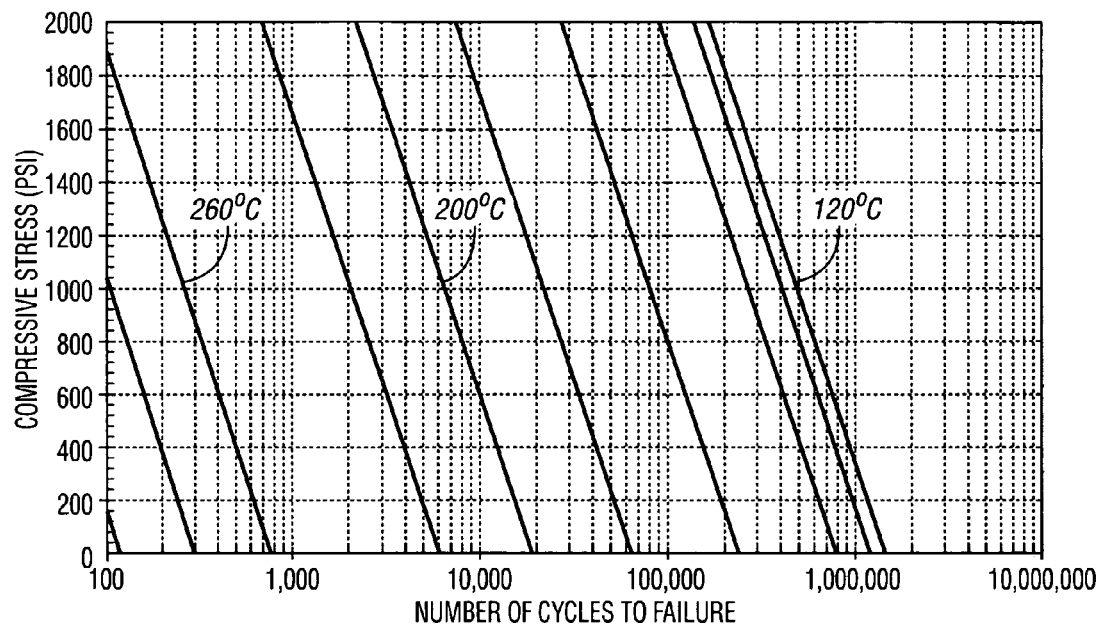
FIG. 4
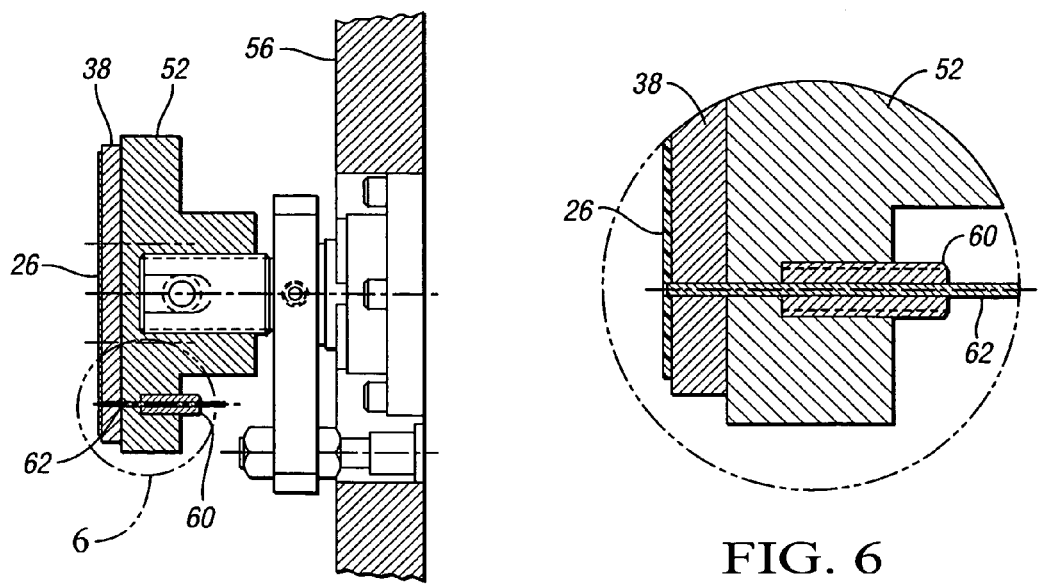
FIG. 5
FIG. 6

COMPRESSIVE FATIGUE AND ENERGY TEST APPARATUS AND METHOD FOR TESTING CLUTCH PLATE FRICTION MATERIALS

TECHNICAL FIELD

The present invention relates to a test apparatus for simultaneously testing the compressive strength and the thermal energy dissipated by a given sample of friction material while engaged with a rotatable reaction plate.

BACKGROUND OF THE INVENTION

Typically manual and automatic vehicle transmissions are equipped with at least one clutching mechanism (or torque transmitting device). The clutch functions to either mechanically link or disconnect two rotating shafts so that they spin at the same angular velocity or at different speeds. The clutch does so by meshing a clutch plate and clutch disc that is lined with a friction material. The more durable (or resistant to failure) the friction material lining the clutch disc is, the longer the clutch will be effective.

There are a plethora of friction materials compatible with vehicle clutch discs made by a variety of manufacturers. Each has its own fatigue life for a given temperature and compressive stress. Therefore, certain friction materials are more suitable for some applications over others. For example, a disc brake may require a friction material that is more durable under high compressive stresses while a transmission gear clutch may require a clutch disc with friction material that is more durable in heated working environments.

As the clutch plate or flywheel rotates it generates kinetic energy equal to its angular velocity, $\omega$, squared multiplied by the clutch plate's mass moment of inertia, $I_m$, divided by two: $W_{rotation} = I_m \omega^2 / 2$. To halt the clutch plate (as done in braking) a compressive energy greater than or equal to the kinetic energy generated by rotation of the clutch plate must be applied to the clutch plate by the clutch disc. The energy of a non-rotating clutch disc is equal to its actual kinetic coefficient of friction, $\mu_k$, multiplied by its mass, m, and its linear velocity, v, squared, divided by two: $W_{linear} = \mu_k m v^2 / 2$. When the application of the clutch disc does not immediately link and alter the rotation of the clutch plate slip occurs. This slip dissipates thermal energy characterized by a temperature change. The thermal energy resulting from slip is equal to the mass, m, of the clutch plate multiplied by its specific heat, c, and the change in temperature, $\Delta T$: $W_{thermal} = mc\Delta T$.

Testing can be performed to measure the compressive strength of the friction material lining the clutch disc, indicating the number of cycles to failure. However, such tests do not account for the rotational energy generated by the clutch plate nor the heat dissipated upon slip.

SUMMARY OF THE INVENTION

A means for simultaneously testing the compressive strength and measuring the thermal energy dissipated by a given sample of friction material during slip is provided. A plurality of test samples are controlled by hydraulically actuated cylinders to selectively interact with a simulated transmission reaction plate.

The apparatus may include a servo valve, operated by a control processing unit, which regulates the elevation of the test samples.

The apparatus may also include a plurality of thermocouples configured to assess the temperature each test sample. Infrared thermal sensors may also be utilized to measure the temperature of the reaction plate as it rotates. This temperature differential is used to measure the heat energy dissipated when the test sample and reaction plate interact. The kinetic coefficient of friction for each of the test samples may be derived accordingly.

The apparatus includes a flywheel, which simulates the relative rotation between a transmission reaction plate and a clutch disc lined with friction material.

The reaction plate may also be thermally insulated by placing an insulation sheet between the reaction plate and its power source or flywheel.

More specifically, a test apparatus for simultaneously testing the compressive strength and the thermal energy dissipated by a given sample of friction material during slip is included with the present invention. The apparatus includes a rotating reaction plate configured to simulate the surface finish and thickness of a transmission reaction plate. Further included are a plurality of support assemblies each adapted to support a test sample and selectively compress at least one of the test samples with respect to the rotating reaction plate, thereby producing slip. A plurality of thermocouples are mounted with respect to the test samples and configured to assess the temperature of the plurality of test samples during testing.

A method of testing friction materials for transmission clutches is also included. The method involves: mounting a plurality of different friction material test samples on hydraulic cylinders; simultaneously hydraulically compressing each test sample at the same pressure against a rotating reaction plate; measuring the temperatures of the test sample and the reaction plate; and storing the respective temperatures of the test samples and the reaction plate in a processing unit. In this arrangement the reaction plate is configured to simulate the same surface finish and thickness as a predetermined transmission reaction plate.

The above features and advantages and other features and advantages of the present invention are readily apparent from the following detailed description of the best mode for carrying out the invention when taken in connection with the accompanying drawings.

BRIEF DESCRIPTION OF THE DRAWINGS

FIG. 4 is a graphical depiction of the performance trends—compressive stress versus number of cycles to failure—at variable temperatures for one test sample;

FIG. 5 is a schematic cross-sectional view of a test sample with thermocouple lodged therebetween; and FIG. 6 is a schematic cross-sectional view of the test sample of FIG. 5 illustrating the encircled portion therein.

DESCRIPTION OF THE PREFERRED EMBODIMENTS

Figure 1:
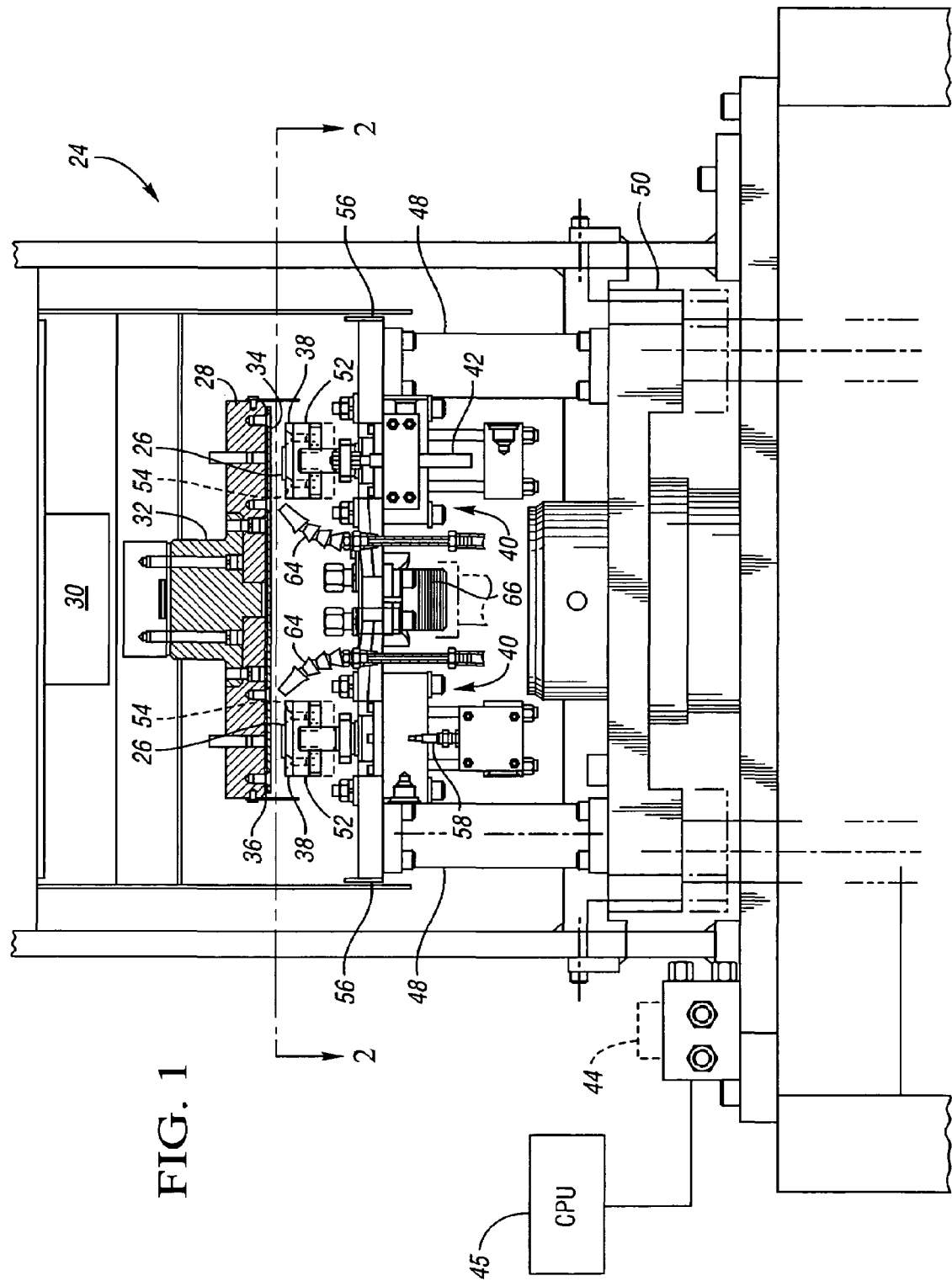
FIG. 1 is a schematic perspective view of the compression and energy test apparatus with individualized support assemblies.

Referring to the drawings, FIGS. 1 through 6, wherein like characters represent the same or corresponding parts throughout the several views there is shown in FIG. 1 is a schematic perspective view of the compression and energy test apparatus 24. Fundamentally, the present invention relates to a test apparatus 24 for simultaneously testing the compressive strength and the thermal energy dissipated by a given sample of friction material during slip. The apparatus 24 includes a rotating reaction plate 34 configured to simulate the surface finish and thickness of a transmission reaction plate. Further included are a plurality of support assemblies 40 each adapted to support a test sample 26 and selectively compress at least one of the test samples with respect to the rotating reaction plate, thereby producing slip. A plurality of thermocouples 60 (as shown in FIGS. 5 and 6) are mounted with respect to the test samples and configured to assess the temperature of the plurality of test samples during testing.

The prior art includes three other test methods for calculating the compressive strength of certain friction materials. In each test a sample of the friction material is placed under compressive stress until it reaches failure, thereby indicating the maximum compressive stress, $\sigma_{max}$, that the friction material can withstand. The first testing apparatus involves a linear actuated disc that distributes a load over one or more friction material samples. The non-rotating disc is connected to a piston-actuated rod, which incrementally applies pressure to the samples. When using multiple samples the pressure applied to the each sample is equal to the force exerted by the disc, $F_d$, divided by the total surface area of each friction material sample, $A_{total} = \Sigma\ A_1, A_2, A_3, \ldots$. Although this arrangement is capable of simultaneously testing multiple samples, upon doing so an uneven load is applied to the samples as some materials fail before others. For example, if one of three samples fails the two remaining samples see the remaining load or pressure equal to $F_d$ divided by $\Sigma\ A_1, A_2$. As one sample fails its load is distributed to those samples capable of withstanding the load until they fail.

This testing apparatus may also include an enclosed oven-heated area. The maximum temperature that the oil reaches stagnant, before reaching its flash point, is 170° Celsius and 195° Celsius before reaching its fire point. However upon slip, clutch arrangements in the transmission can see temperatures in excess of 250° Celsius due to energy generation. Since the disc in the testing apparatus does not rotate or generate slip the apparatus is incapable of reproducing the warmer thermal conditions.

The second arrangement includes a plurality of hydraulic cylinders configured to apply an individual compressive stress on each of the samples. Each cylinder has its own pressure line to pressurize the cylinder and compress the samples at the same loads. Though this eliminates the problem of uneven load distribution when a sample material prematurely fails, the configuration does not test the samples under heated conditions in excess of 150° Celsius. Moreover, as true for each of the arrangements, the testing machines only test the compressive strength of the friction material. Neither account for clutch slip as neither arrangement includes any rotating members. Therefore, neither provides for the measurement of the actual coefficient of friction for a given material.

Reaction plates are stationary and thermocoupled in clutch machines. The new machine of the present invention obtains friction material temperature instead of reaction plate temperature, which can not be accomplished in a clutch machine since the friction material clutch plates rotate and the steel reaction plates are stationary. The new machine allows for the possibility of testing different materials at the different stations during experimentation of coefficient of frictions in each material. The existing clutch machines have a stacked plate configuration and the clutch plate friction materials must be the same for valid data to be obtained. Essentially, the new machine has stations that are individually loaded with the same conditions for each apply while the clutch machines only have one actuator driving the force through the stacked configuration—which may or may not necessarily be uniformly loaded in regards to the first plate versus the last plate or the other intermediate plates. Based on prior test results and field results, the first plate (piston side) does show different wear than the last plate or other plates in the stack at times.

One technical advantage of the present invention is that the test apparatus 24 simultaneously tests the compressive strength of a plurality of friction samples 26 and the thermal energy dissipated by the test samples during operation. The test apparatus 24, as shown in FIG. 1, includes a rotatable flywheel 28 capable of rotating at speeds similar to a clutch disc in an operating vehicle transmission. The flywheel 28 is attached to an upper support 30 through a spindle 32. Attached to the flywheel 28 is a polished steel reaction plate 34 having the same surface finish and thickness as a transmission reaction plate. The steel reaction plate 34 rotates with the flywheel 28 during testing. In the shown embodiment, a thermally insulated plate 36 is included between the flywheel 28 and reaction plate 34. The insulated plate 36 serves to maintain the heat in the reaction plate 34 during testing and insulate the heat from the flywheel 28. Without the insulated plate 36 a significant amount of thermal energy may be lost between the reaction plate 34 and the flywheel 28.

Figures 3A, 3B:
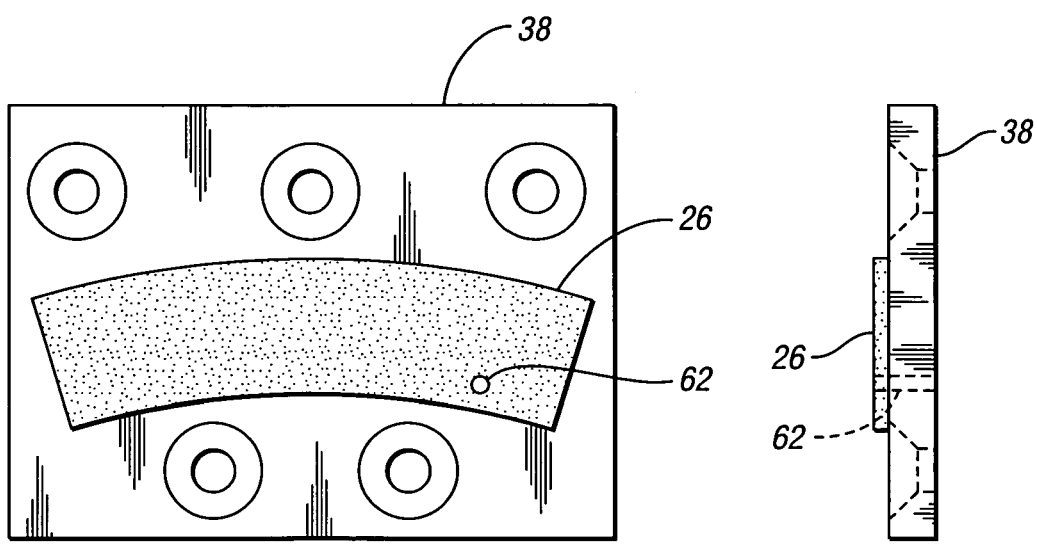
FIG. 3a is a schematic top view of a test sample.
FIG. 3b is a schematic cross-sectional view of a test sample.

The test samples 26 are mounted to a sample plate 38, as illustrated in FIGS. 3a and 3b. Each test sample 26 is cut into an arched or semi-annular shape to simulate the configuration of a transmission friction plate. The test samples 26 represent the same area as a friction plate in a transmission. The test samples 26 have the same inner and outer radius as a transmission friction plates as well. Therefore, the test samples 26 essentially represent a segmented friction plate allowing for multiple samples to simultaneously interact with the reaction plate 34 of FIG. 1.

Subjacent the flywheel 28, a plurality of friction samples 26 are mounted to hydraulically actuated support assemblies 40, as shown in FIG. 1. The multiple sample array allows the hydraulic cylinders 42 to test one sample of each friction material independent of the performance of the other samples. If one sample begins to wear, the other samples will not redistribute the load; instead all samples will see the same load regardless of one sample wearing faster than the remaining samples. A high frequency servo valve 44 and feedback control software for a control processor 45 governs the hydraulic cylinders 42. The feedback allows the hydraulic cylinders 42 to all equally pressurize and lift the test samples 26 to simultaneously contact the reaction plate 34. The valve supplies pressurize air (or fluid) into the cylinders through their respective pressure lines. The servo valve is selectively programmable to apply the same load against each test sample 26 or variable loads. The arrangement of the hydraulically actuated support assemblies 40 may be vertically adjusted. Each are anchored in a riser column 48, which is secured to an adjustable height bedplate 50. As the bedplate 50 is adjusted vertically the support assemblies 40 also adjust to accommodate differently sized test samples 26 or a larger flywheel. The support assemblies 40 include a fixture block 52 to which the test samples 26 may be secured by a plurality of structural connectors 54. The fixture block 52 is configured to receive the structural connectors 54. Under the fixture block 52 is a cylinder support plate 56, which is mechanically linked to the piston 58 of the hydraulic cylinders 42 (as shown in FIG. 1). When pressurized the hydraulic cylinders 42 elevate the cylinder support plate 56, fixture block 52 and test samples 26 against the flywheel 28. The test samples 26 are compressed against the flywheel 28 until failure and the compressive strength of each material is measured accordingly.

FIG. 4, illustrates a schematic representation of a graph of the compressive stress of one material sample versus the number of cycles to failure, for a given temperature. In testing, a log may be kept of the number of cycles to failure for a particular sample of material at different temperatures. From two or more data points within a given operating temperature a line is extrapolated to predict the cycles to failure for each given sample. For example, if the friction material for which this graph represents will see operating temperature of 180° Celsius and compressive stresses of 600 psi, the material will last approximately 50,000 cycles before failing. These data points can be used to develop an analytical math model of the stress versus life curves for each of the various friction materials at different operating temperatures and pressures. The math model can be utilized for as a bill-of-design (or material specification) reference and other developmental aspects of designing clutch plates with different friction materials.

Another technical benefit of measuring the thermal energy dissipated during slip for each test sample is that the actual kinetic coefficient of friction, $\mu_k$, for each sample can be assessed for a given friction material. The reaction plate 34 is configured with enough rotational energy to produce slip when interacting with the friction samples 26. High temperatures are generated by this slip, which cannot be generated by statically heating the transmission fluid. The temperatures generated from slip in this test are closely related to the actual temperatures achieved during shifting in a vehicle transmission. The thermal energy dissipated by each sample 26 is equal to the difference between the rotational energy produced by the flywheel 28 and reaction plate 34 and the kinetic energy provided by the compression of the test samples 26 against the reaction plate 34, not considering any minor system losses. Given that the rotational energy produced by flywheel 28 is consistent between the samples, the lower the temperature differential is between the test sample 26 and the reaction plate 34, the greater the kinetic coefficient of friction will be for that sample. The actual kinetic coefficient of friction for a sample of material is approximated through the following expression for each of the given samples:

$$\mu_{k_{sample\_x}} = \frac{I_m \omega^2}{mv^2} - \frac{2c|(T_{reactionplate} - T_{sample\_x})|}{v^2}.$$

Figure 2:
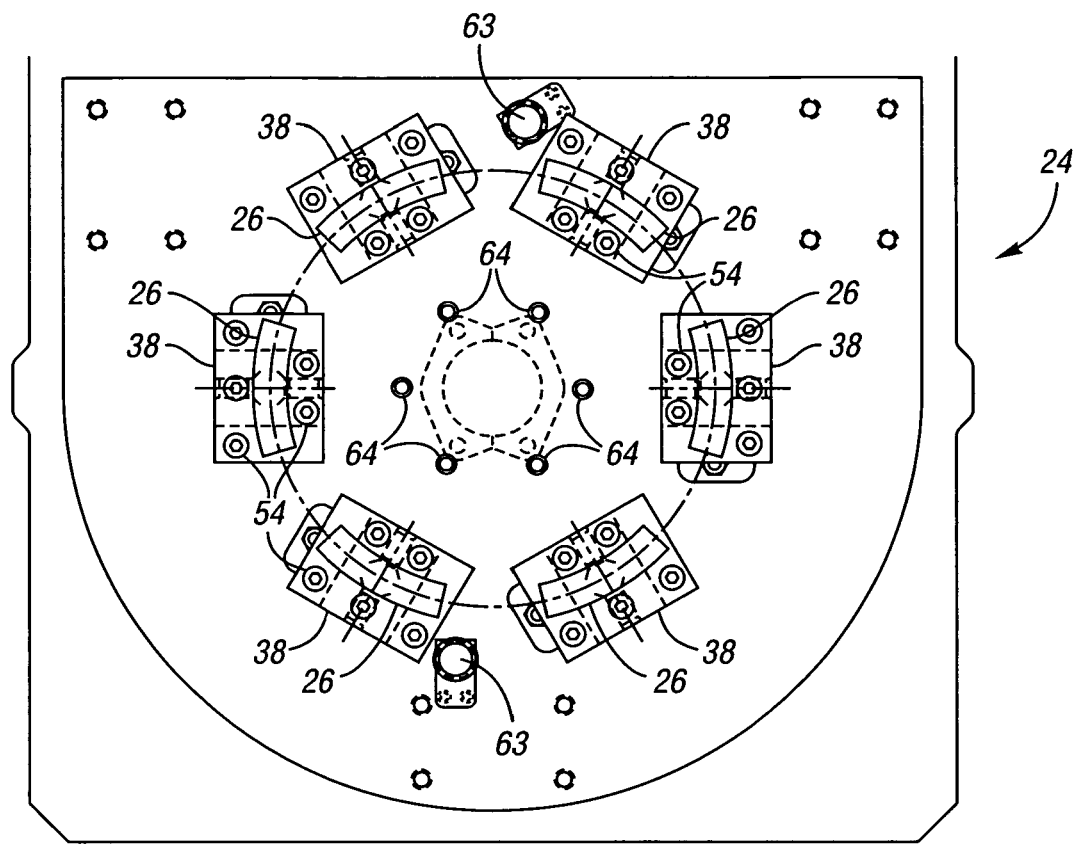
FIG. 2 is a schematic top view of the compression and energy test apparatus in fragmentary cross-sectional view taken along line 2-2 of FIG. 1.

The temperature of the friction material samples is taken by an internal thermocouple 60 utilized in a small aperture 62 extending through the test sample 26, as shown in FIGS. 5 and 6. The temperature of the reaction plate 34 at each location is measured by an infrared thermal sensor 63, as shown in FIG. 2. Since the preferred embodiment tests under wet conditions this estimated coefficient of friction, $\mu_k$, takes the cooling effects provided by the lubricant oil into consideration. Oil is fed into the apparatus 24 through oil supply lines 64 and drained through a lube drain fixture 66 for recycle or disposal.

The test machine 24 may also generate data for applications having different reaction plates 34. The flywheel 28 may have a higher angular velocity for applications in which the clutch plate rotates at higher speeds; or the dimensions of the reaction plate 34 may be altered thereby altering the mass moment of inertia of the flywheel assembly.

Furthermore, the present invention also provides a method of testing friction materials for transmission clutches. The method involves: simultaneously hydraulically compressing each test sample at the same pressure against a rotating reaction plate 34; measuring the temperatures of the test sample 26 and the reaction plate 34; and storing the respective temperatures of the test samples and the reaction plate in a processing unit 45. In the arrangement the reaction plate is configured to simulate the same surface finish and thickness as a predetermined transmission reaction plate.

While the best modes for carrying out the invention have been described in detail, those familiar with the art to which this invention relates will recognize various alternative designs and embodiments for practicing the invention within the scope of the appended claims.

The invention claimed is:

1. A test apparatus, comprising:
   a rotating reaction plate configured to simulate the surface finish and thickness of a transmission reaction plate;
   a plurality of support assemblies adapted to support test samples and to selectively compress at least one of the test samples with respect to said rotating reaction plate, thereby producing slip; and
   a plurality of thermocouples mounted to said support assemblies and configured to assess the temperature of the test samples during testing such that the apparatus simultaneously tests the compressive strength and the thermal energy dissipated by a given test sample of friction material during slip.

2. The test apparatus of claim 1, further comprising:
   a plurality of hydraulic cylinders secured with respect to said support assemblies operative to selectively simultaneously elevate at least two of the test samples.

3. The test apparatus of claim 2, further comprising:
   a servo valve, controlled by a control processing unit, configured to regulate the selective elevation of said plurality of hydraulic cylinders.

4. The test apparatus of claim 1, further comprising:
   an infrared thermal sensor operable to assess the temperature of said reaction plate while in rotational motion.

5. The test apparatus of claim 4, wherein said infrared sensor is configured to send a signal to a control processing unit indicative of the assessed temperature.

6. The test apparatus of claim 5, wherein said control processing unit is configured to calculate the kinetic coefficient of friction for the test samples from the assessed temperatures.

7. The test apparatus of claim 6, further comprising:
   a flywheel by which said reaction plate is powered and secured; and
   a thermal insulation plate secured between said flywheel and said reaction plate.

8. A friction material testing apparatus, comprising:
- a flywheel configured to rotate at a predetermined speed;
- a reaction plate secured with respect to said flywheel, said reaction plate simulating the surface finish and thickness of a transmission reaction plate; and
- a plurality of hydraulic actuators adapted to support friction material test samples;

wherein said hydraulic actuators are configured to selectively engage the friction material test samples with said reaction plate for simultaneous testing of compressive strength and dissipation of thermal energy during slip.

9. The testing apparatus of claim 8, further comprising:
- a servo valve, controlled by a control processing unit, configured to regulate the selective engagement of the friction material test samples and said reaction plate.

10. The testing apparatus of claim 9, further comprising:
- a plurality of thermocouples some of which are mounted with respect to the friction material test samples.

11. The testing apparatus of claim 10, wherein said plurality of thermocouples are configured to selectively assess the temperature of the friction material test samples during testing.

12. The test apparatus of claim 11, further comprising:
- a thermally insulated plate secured between said flywheel and said reaction plate;

wherein at least one of said plurality of thermocouples is an infrared thermocouple operable to assess the temperature of said reaction plate while rotating.

13. The test apparatus of claim 12, wherein said plurality of said thermocouples are configured to send a signal to a processing unit; said signal indicative of the assessed temperature; and wherein said processing unit is configured to calculate the kinetic coefficient of friction for the friction material test samples from the assessed temperatures.

14. A method of testing the compressive strength of a given friction material at various temperatures, comprising:
- simultaneously hydraulically compressing a plurality of test samples at the same pressure against a rotating reaction plate, said reaction plate simulating the same surface finish and thickness as a predetermined transmission reaction plate;
- measuring the temperatures of each of said plurality of test samples and said reaction plate;
- storing the respective temperatures of said test samples and said reaction plate in a processing unit; and
- measuring the maximum compressive strength of said test samples and the number of cycles to failure for each of said test samples at each of the variable temperatures.

15. The method of claim 14, further comprising:
- calculating the coefficient of friction for said test samples from said measuring the temperatures of said test samples and said reaction plate.

16. The method of claim 15, further comprising:
- storing the coefficient of friction for said test samples, the measured temperatures of said test samples and the compressive strength of said test samples; and
- creating a mathematical model for predicting the failure mode of said test samples accordingly.

* * * * *